United States Patent [19]

Leigh

[11] Patent Number: 4,683,089
[45] Date of Patent: Jul. 28, 1987

[54] CYCLOPROPANE CARBOXYLIC ACID DERIVATIVES

[75] Inventor: Thomas Leigh, Macclesfield, England

[73] Assignee: Imperial Chemical Industries Limited, London, England

[21] Appl. No.: 86,036

[22] Filed: Oct. 18, 1979

[30] Foreign Application Priority Data

Oct. 27, 1978 [GB] United Kingdom ............... 42266/78

[51] Int. Cl.$^4$ ............................................. C07C 61/04
[52] U.S. Cl. ................................ 260/501.16; 562/401; 562/506
[58] Field of Search ............................... 562/401, 506; 260/501.16

[56] References Cited

U.S. PATENT DOCUMENTS

| | | | |
|---|---|---|---|
| 3,786,070 | 1/1974 | Martel et al. | 562/506 X |
| 3,842,125 | 10/1974 | Horiuchi et al. | |
| 3,879,451 | 4/1975 | Yoshioka et al. | 562/506 X |
| 3,892,814 | 7/1975 | Raphael et al. | 562/506 X |
| 3,979,519 | 9/1976 | Punja | 562/506 X |
| 4,118,417 | 10/1978 | Epstein | 562/401 |
| 4,229,593 | 10/1980 | Kondo et al. | 562/401 |

FOREIGN PATENT DOCUMENTS 1270270 4/1972 United Kingdom .
1369730 10/1974 United Kingdom .
1448228 9/1976 United Kingdom .
1491408 11/1977 United Kingdom .
2015519 9/1979 United Kingdom .

Primary Examiner—Werren B. Lone
Assistant Examiner—Vera C. Clarke
Attorney, Agent, or Firm—Cushman, Darby & Cushman

[57] ABSTRACT

A process for separating the individual optically active isomers of cis- or trans-forms of cyclopropane carboxylic acids of formula:

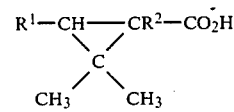

wherein $R^1$ is halo, alkyl, alkenyl, haloalkyl, haloalkenyl or haloalkynyl, and $R^2$ is hydrogen or cyano, from a mixture of cis-isomers or trans-isomers which comprises treating an aqueous solution of a soluble salt of the racemate or diastereoisomeric mixture of the cis- or trans-isomers with just sufficient of a single isomer of an optically active amine to cause precipitation of one isomer or diastereoisomer of the cyclopropane carboxylic acid as the ammonium salt while substantially all of the other isomer remains in solution as the soluble salt.

2 Claims, No Drawings

CYCLOPROPANE CARBOXYLIC ACID DERIVATIVES

This invention relates to the separation of individual optically active isomers of cyclopropane carboxylic acids from mixtures of such isomers.

Cyclopropane carboxylic acids of the general formula:

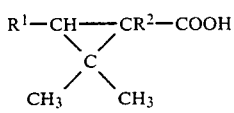

wherein $R^1$ is halo, alkyl, alkenyl, haloalkyl, haloalkenyl, or haloalkynyl, and $R^2$ is hydrogen or cyano are intermediates for the preparation of insecticides, including for example, the 3-phenoxybenzyl and α-cyano-3-phenoxybenzyl esters of the following cyclopropane carboxylic acids.

3-(2-methylpropenyl)-2,2-dimethylcyclopropane carboxylic acid,
3-(2,2-dichlorovinyl)-2,2-dimethylcyclopropane carboxylic acid,
3-(2,2-dibromovinyl)-2,2-dimethylcyclopropane carboxylic acid,
3-(2-chloro-3,3,3-trifluoropropenyl)-2,2-dimethylcyclopropane carboxylic acid,
3-(2-bromo-3,3,3-trifluoropropenyl)-2,2-dimethylcyclopropane carboxylic acid,
3-(2-trifluoromethyl-3,3,3-trifluoropropenyl)-2,2-dimethylcyclopropane carboxylic acid,
and other similar acids.

The cyclopropane carboxylic acids of the above general formula may exist in four individual isomeric forms, which may conveniently be specified as (1S, cis), (1S, trans), (1R, cis) and (1R, trans), as depicted in the following formulae:

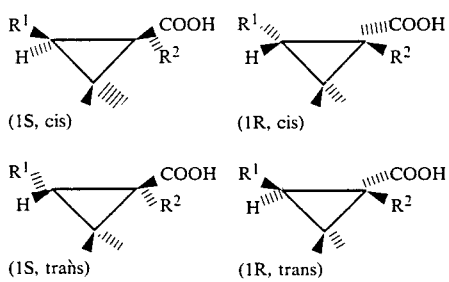

The insecticidal esters derived from these individual isomers have differing insecticidal properties, and frequently one isomeric form of the ester is outstandingly more effective than the others or the mixtures thereof obtained by conventional synthesis. Although it may be possible to effect separation of the isomeric insecticidal esters by for example high performance liquid chromatographic techniques, it is more economic to separate the isomers of the intermediate cyclopropane carboxylic acids. Various methods involving the classical resolution techniques of fractional crystallisation of the mixed salts of the various isomeric acids with optically active amines in organic solvents are not very satisfactory in practice because of the small differences in solubility between the various salts.

This invention concerns a novel approach to the problem of separating the various isomers which uses inexpensive and readily available reagents.

Accordingly the present invention provides a process for separating the individual optically active isomers of cis- or trans-forms of cyclopropane carboxylic acids of formula:

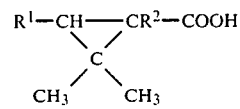

wherein $R^1$ is halo, alkyl, alkenyl, haloalkyl, haloalkenyl, or haloalkynyl, and $R^2$ is hydrogen or cyano from a mixture of cis-isomers or trans-isomers, which comprises the step of treating an aqueous solution of a soluble salt of the racemate or diastereoisomeric mixture of the cis- or trans-isomers with just sufficient of a single isomer of a suitable optically active amine to cause precipitation of one isomer or diastereoisomer of the cyclopropane carboxylic acid as the ammonium salt whilst substantially all of the other isomer (or isomers if more than two are present) remains in solution as the soluble salt.

Suitable optically active amines are those which form insoluble salts with either or both of the cis-isomers or trans-isomers which it is desired to separate. A preferred class of such amines are α-alkylated benzylamines for example, 1-α-methylbenzylamine. It is convenient to employ the amine at a rate of one mole for every two moles of the cis- or trans-cyclopropane carboxylic acids present. Suitable soluble salts of the cyclopropane carboxylic acids are preferably alkali metal salts, and salts with metals which do not form insoluble complexes with the optically active amine used in the process.

After precipitation the ammonium salt of the optically active isomer of the cyclopropane carboxylic acid may be collected by filtration, and the acid recovered by treatment with mineral acid, e.g. hydrochloric acid, the amine being recovered for reuse in the separation process.

The ammonium salts sometimes form very voluminous precipitates and care should be taken to ensure that the process is conducted at sufficiently high dilution to enable the precipitated product to be easily separated by filtration. The concentration of the soluble salts of the cis- or trans-cyclopropane carboxylic acids should preferably be a rate of about 2 to 6% by weight with respect to the acid. However, the problem of dilution can be overcome to some extent if a miscible solvent is present with the water, for example on a lower saturated aliphatic alcohol, such as methanol, especially if the addition of amine is carried out at a slightly elevated temperature, for example in the range 50° to 80° C. Under these conditions the precipitated salt is formed in a more crystalline state and is easier to collect by filtration than the more voluminous product obtained when water alone is used. The term "aqueous" as used herein, unless the context clearly requires otherwise, includes water and water-containing mixtures of solvents.

If it is required to separate a single isomer from a mixture of the two cis- and two trans-isomers a preliminary separation of cis- and trans-isomers is sometimes desirable. Although any method of separating cis- and trans-isomers may be used, e.g. fractional crystallisation, of the acids themselves, fractional distillation of lower alkyl esters, or by chemical techniques involving the selective lactonisation of the cis acid or derivatives thereof, it is especially convenient to utilise a selective precipitation technique which comprises treating an aqueous solution of a soluble salt of the cis- and trans-isomers with just sufficient of an acid to cause precipitation of one isomeric form of the cyclopropane carboxylic acid whilst substantially all or a major proportion of the other isomeric form remains in solution as the soluble salt.

Although any acid having a $pK_a$ which is lower than the $pK_a$ of the isomeric form of the cyclopropane carboxylic acid to be precipitated may be used it is especially preferred to use an acid which has a $pK_a$ which is not lower than the $pK_a$ of the isomeric form of the cyclopropane carboxylic acid which is to remain in solution as the soluble salt since treatment by excess of the acid will not result in unwanted precipitation of that isomeric form. If an acid of lower $pK_a$ is used then the end point of the precipitation of the isomeric form of the cyclopropane carboxylic acid with the higher $pK_a$ should be determined by following the change of pH of the aqueous mixture, or by calculation of the amount of acid to be added when the actual quantities of the cis and trans-isomers in a particular mixture is known.

The term "acid" as used in relation to the substance which causes the precipitation of cyclopropane carboxylic acid is intended to embrace any substance which when added to the aqueous solution of the soluble salts of the cyclopropane carboxylic acids causes the pH to be lowered sufficiently to cause precipitation of at least one of the isomeric forms of the cyclopropane carboxylic acid. Acids which may be employed include carboxylic acids such as formic acid, acetic acid, propionic acid, and butyric acid, sulphonic acids such as benzene sulphonic acid and toluene sulphonic acid, inorganic mineral acids such as sulphuric acid, hydrochloric acid, nitric acid and phosphoric acid. One particularly useful acid is carbonic acid which is produced by passing in carbon dioxide gas or by adding solid carbon dioxide to the solution of soluble salts.

Suitable soluble salts are preferably ammonium salts and alkali metal salts, and the aqueous solution of soluble salts may be prepared by dissolving the cyclopropane carboxylic acids in an aqueous solution of the hydroxide.

After precipitation the isomeric form of the cyclopropane carboxylic acid may be collected by filtration, and further purified if necessary by crystallisation from an appropriate solvent, although in many cases it will be possible to use the product without any further purification.

The invention processes are illustrated by the following Examples. It is to be understood that the following Examples describe experimental procedures designed to evaluate the scope of the invention process and the conditions used in any particular case are not necessarily those which would lead to the optimum yield or purity of product.

EXAMPLE 1

A mixture of isomeric cyclopropane carboxylic acids (482 g) of the following composition as determined by N.M.R. spectrum measurement, (±)-cis-3-[(Z)-2-chloro-3,3,3-trifluoroprop-1-en-1-yl]-2,2-dimethylcyclopropane carboxylic acid (61%), (±)-trans-3-[(Z)-2-chloro-3,3,3-trifluoroprop-1-en-1-yl]-2,2-dimethylcyclopropane carboxylic acid (34%), (±)-cis-3-[(E)-2-chloro-1,1,1-trifluoroprop-1-en-1-yl]-2,2-dimethylcyclopropane carboxylic acid (2%) and (±)-trans-3-[(E)-2-chloro-3,3,3-trifluoroprop-1-en-1-yl]-2,2-dimethylcyclopropane carboxylic acid (3%) is dissolved in N sodium hydroxide (2 1). Carbon dioxide is passed into the stirred solution until no further precipitation of solid occurs. The mixture is filtered and the residue is washed with water. The solid is dried to obtain almost pure (>95%) (±)-cis-3-[(Z)-2-chloro-3,3,3-trifluoroprop-1-en-1-yl]-2,2-dimethylcyclopropane carboxylic acid (250 g), m.p. 108° C.

EXAMPLE 2

In a similar experiment to that described in Example 1 dilute (2N) acetic acid (500 cc) was added dropwise over a period of one hour in place of the addition of carbon dioxide. This also resulted in selective precipitation of (±)-cis-3-[(Z)-2-chloro-3,3,3-trifluoroprop-1-en-1-yl]-2,2-dimethylcyclopropane carboxylic acid.

EXAMPLE 3

A mixture of isomeric cyclopropane carboxylic acids (20.9 g) consisting of approximately equal proportions of (±)-cis-3-(2,2-dichlorovinyl)-2,2-dimethylcyclopropane carboxylic acid and (±)-trans-3-(2,2-dichlorovinyl)-2,2-dimethylcyclopropane carboxylic acid was added to a stirred solution of sodium hydroxide (4.0 g) in water (200 ml) and the mixture obtained stirred for 30 minutes, treated with charcoal (3.0 g) and stirred for a further 30 minutes, after which the charcoal and other minor insoluble impurities were removed by filtration. A stream of carbon dioxide gas was passed into the stirred filtrate over a period of 3 hours during which time a white solid was precipitated. The precipitate was collected by filtration, washed with water and dried at the ambient temperature, and shown by proton nuclear magnetic resonance spectroscopy to be a mixture (7.1 g) consisting of 80% by weight of the (±)-cis acid and 20% by weight of the (±)-trans acid, having a melting point of 70°–72° C. The mixture was dissolved in a freshly prepared solution of sodium hydroxide (1.4 g) in water (100 ml), and carbon dioxide gas passed into the solution until precipitation appeared to be complete. The precipitate was collected by filtration washed with water and air dried. N.m.r. spectroscopy indicated it to be a mixture consisting of 98% of (±)-cis-3-(2,2-dichlorovinyl)-2,2-dimethylcyclopropane carboxylic acid and 2% of the (±)-trans acid, melting at 80°–82° C.

EXAMPLES 4–12

A series of further experiments was carried out using the general procedure of Example 3 but differing in the cis/trans ration of the starting material [(±)-cis/trans-3-(2,2-dichlorovinyl)-2,2-dimethylcyclopropane carboxylic acid], the dilution factor (expressed as millilitres of water used to prepare the sodium hydroxide solution per gram of starting material), molar scale and time of injecting carbon dioxide into the solution. The experimental details and results obtained are summarised in the following Table.

| EXAMPLE NO | MOLAR SCALE | DILUTION FACTOR | INJECTION TIME (HRS) | CIS/TRANS RATIO % | | % WT. OF RECOVERED PRECIPITATE |
|---|---|---|---|---|---|---|
| | | | | STARTING MATERIAL | RECOVERED PRECIPITATE | |
| 4 | 0.1 | 19 | 3 | 50/50 | 90/10 | 28 |
| 5 | 0.5 | 9.6 | 3 | 50/50 | 90/10 | 30 |
| 6 | 0.5 | 19 | 3 | 50/50 | 92/8 | 32 |
| 7 | 0.25 | 9.6 | 3 | 40/60 | 80/20 | 33 |
| 8 | 0.5 | 4.8 | 4 | 40/60 | 92/8 | 15 |
| 9 | 0.5 | 19 | 4 | 40/60 | 92/8 | 33 |
| 10 | 0.08 | 10 | 3 | 80/20 | 98/2 | 47 |
| 11 | 0.36 | 10 | 3 | 90/10 | 100/0 | 54 |
| 12 | 0.08 | 10 | 3 | 92/8 | 98/2 | 47 |

EXAMPLE 13

To a stirred solution of (±)-cis-3-[(Z)-2-chloro-3,3,3-trifluoroprop-1-en-1-yl]-2,2-dimethylcyclopropane carboxylic acid (1.2 g) in 0.2 N sodium hydroxide (25 cc) is added dropwise during 15 minutes a solution of 1-α-methylbenzylamine (0.3 g) in 0.2 N hydrochloric acid (12.5 cc). The mixture is filtered and the residue is washed with water. The solid is dried (0.70 g), it consists of the 1-α-methylbenzylamine salt of (±)-cis-3-[(Z)-2-chloro-3,3,3-trifluoroprop-1-en-1-yl]-2,2-dimethylcyclopropane carboxylic acid, m.p. 173°. The salt is stirred with a mixture of 2N hydrochloric acid (5 cc) and dichloromethane (5 cc). The dichloromethane solution is separated and it is washed with water. The dichloromethane is distilled and the residue is (±)-cis-3-[(Z)-2-chloro-3,3,3-trifluoroprop-1-en-1-yl]-2,2-dimethylcyclopropane carboxylic acid, $[\alpha]_D^{25}$ (C, 5, chloroform) +45°. The pure isomer has $[\alpha]_D^{25}$ (C, 5, chloroform) +48°.

EXAMPLE 14

A mixture of isomeric cyclopropane carboxylic acids (2.4 g) of the following compositions as determined by NMR spectrum measurement, (±)-cis-3-[(Z)-2-chloro-3,3,3-trifluoroprop-1-en-1-yl]-2,2-dimethylcyclopropane carboxylic acid (61%), (±)-trans-3-[(Z)-2-chloro-3,3,3-trifluoroprop-1-en-1-yl]-2,2-dimethylcyclopropane carboxylic acid (34%), (±)-cis-3-[(E)-2-chloro-3,3,3-trifluoroprop-1-en-1-yl]-2,2-dimethylcyclopropane carboxylic acid (2%) and (±)-trans-3-[(E)-2-chloro-3,3,3-trifluoroprop-1-en-1-yl]-2,2-dimethylcyclopropane carboxylic acid (3%) is dissolved in 0.2 N sodium hydroxide (50 cc). To the stirred solution is added dropwise during fifteen minutes a solution of 1-α-methylbenzylamine (0.3 g) in 0.2 N hydrochloric acid (12.5 cc). The mixture is filtered and the residue is washed with water to obtain the 1-α-methylbenzylamine salt (0.6 g) of (+)-cis-3-[(Z)-2-chloro-1,1,1-trifluoro-2-propenyl]-2,2-dimethylcyclopropane carboxy acid, m.p. 168° C. The pure salt (0.5 g), m.p. 174°, is obtained by crystallisation from isopropanol. The cyclopropanecarboxylic acid is then isolated as described for Example 3.

EXAMPLE 15

A solution of 1-α-methylbenzylamine (6.05 g, 0.05M) in water (50 ml) containing hydrochloric acid (37% w/w, 4.93 g, 0.05M) was preheated to 60°–65° C. and added rapidly to a well stirred solution of the sodium salt of (±)-cis-3-[(Z)-2-chloro-3,3,3-trifluoro-2-prop-1-en-1-yl]-2,2-dimethylcyclopropane carboxylic acid (prepared by adding the acid (24.25 g, 0.1M) to a solution of sodium hydroxide (4.0 g, 0.1M) in a mixture of water (50 ml) and methanol (100 ml) also maintained at 60°–65° C. The mixture thus obtained was allowed to cool over a period of 2 hours during which time stirring was continued. The solid precipitate was collected by filtration, washed with a mixture of water and methanol (50/50 v/v) and drained. (The filtrate and washings on treatment with aqueous hydrochloric acid yielded a precipitate which was shown by nuclear magnetic resonance spectroscopy to consist principally of the (−) cis isomer).

The filtercake was added in portions to a stirred mixture of water (50 ml) and hydrochloric acid (37% w/w, 4.93 g, 0.05M) and the stirring continued for a further 30 minutes. The precipitated product was collected by filtration, washed with water, and dried. The filtrate and washings contain regenerated 1-α-methylbenzylamine hydrochloride which can be reused with fresh starting material. The product was dried by dissolving in chloroform and treating with anhydrous magnesium sulphate, followed by filtration and evaporation of the solvent to yield 7.7 g of a white powdery solid identified by nuclear magnetic resonance spectroscopy as (+)-cis-3-[(Z)-2-chloro-3,3,3-trifluoroprop-1-en-1-yl)]-2,2-dimethylcyclopropane carboxylic acid, melting point 105°–106° C. (yield 64%). The optical purity was shown to be approximately 100% by nuclear magnetic spectroscopic examination of the —OCH$_3$ proton signal (ea τ6.3) of the methyl ester obtained by esterifying the product with diazomethane, and recording the spectrum in deutero-chloroform in the presence of a shift reagent (europium tris-3D-heptafluorobutyryl camphorate).

EXAMPLE 16

The procedure of Example 15 was repeated using 0.4M of starting material, giving a yield of 72%. The recovered 1-α-benzylamine hydrochloride solution was estimated spectrophotometrically as containing 60% of its original charge and after making up to 0.2M it was used to resolve a further 0.4M charge of (±)-cis-3-[(Z)-2-chloro-3,3,3-trifluoroprop-1-en-1-yl]-2,2-dimethylcyclopropane carboxylic acid, yielding the (±)-cis acid in 62% of the theoretical amount.

EXAMPLE 17

A sample of (±) cis-3-(2,2-dichlorovinyl)-2,2-dimethylcyclopropane carboxylic acid (10.45 g, 0.05M, purity 98% w/w) was added in portions to a stirred solution of sodium hydroxide (2.0 g, 0.05M) in water (50 ml) and the solution obtained filtered to remove a minor amount of insoluble impurity. To the filtrate was added (in portions over a period of 7 minutes) a solution of 1-α-methylbenzylamine hydrochloride prepared by adding the amine (3.03 g, 0.025M) to a mixture of water (25 ml) and hydrochloric acid (37% w/w, 2.47 g, 0.025). This resulted in the formation of a voluminous white precipitate, which was collected by filtration after the addition of more water (100 ml) to the mixture and standing for 10 minutes. The solid was washed with water (2×50 ml) slurried with water (100 ml) and refiltered, and rewashed with water (2×50 ml). The damp filtrate was then added in positions to a stirred mixture of water (25 ml), hydrochloric acid (37% w/w, 2.47 g, 0.025M) and dichloromethane (30 ml) at the ambient temperature. When the addition was complete and all the solid had dissolved the phases were separated. The aqueous phase was extracted with dichloromethane (2×25 ml) and the extracts combined with organic phase. The dichloromethane solution was dried over anhydrous sodium sulphate, the solids removed by filtration, and the solvent removed from the filtrate by evaporation under reduced pressure at 40° C. The white solid residue (3.75 g, m.p. 7678° C., $/\alpha/_D{}^{20} = +50.6$) was shown, by nuclear magnetic resonance spectroscopic examination of the methyl esters, to be a mixture consisting of a major proportion of the ($\pm$)-cis acid and a minor proportion of the ($-$)-cis acid.

I claim:

1. The 1-α-methylbenzylamine salt of (+)-cis-3-(2-chloro-3,3,3-trifluoroprop-1-en-1yl)-2,2-dimethylcyclopropane carboxylic acid.

2. (+)-cis-3-(2-Chloro-3,3,3-trifluoroprop-1-en-1yl)-2,2-dimethylcyclopropane carboxylic acid.

* * * * *